United States Patent [19]

Thompson et al.

[11] Patent Number: 5,048,340
[45] Date of Patent: Sep. 17, 1991

[54] SEMI-AUTOMATIC SYSTEM FOR ULTRASONIC MEASUREMENT OF TEXTURE

[75] Inventors: R. Bruce Thompson; Samuel J. Wormley, both of Ames, Iowa

[73] Assignee: Iowa State University Research Foundation, Inc., Ames, Iowa

[21] Appl. No.: 485,178

[22] Filed: Feb. 26, 1990

Related U.S. Application Data

[63] Continuation of Ser. No. 197,763, May 23, 1988, abandoned.

[51] Int. Cl.$^5$ .............................................. G01N 29/00
[52] U.S. Cl. ........................................ 73/597; 73/602
[58] Field of Search ................. 73/597, 598, 602, 643, 73/644, 645

[56] References Cited

U.S. PATENT DOCUMENTS

| | | | |
|---|---|---|---|
| 3,720,098 | 3/1973 | Dixon | 73/67.7 |
| 3,981,184 | 9/1976 | Matay | 73/67.8 S |
| 4,218,924 | 8/1980 | Fortunko et al. | 73/643 |
| 4,301,684 | 11/1981 | Thompson et al. | 73/602 |
| 4,366,712 | 1/1983 | Bathmann et al. | 73/600 |
| 4,399,702 | 8/1983 | Suzuki | 73/597 |
| 4,462,082 | 7/1984 | Thiele et al. | 364/571 |
| 4,574,634 | 3/1986 | Pappano | 73/597 |
| 4,790,188 | 12/1988 | Bussiere et al. | 73/597 |
| 4,899,589 | 2/1990 | Thompson et al. | 73/597 |

FOREIGN PATENT DOCUMENTS

| | | |
|---|---|---|
| 2909902 | of 0000 | Fed. Rep. of Germany . |
| 489018 | of 0000 | U.S.S.R. . |
| 489036 | 2/1976 | U.S.S.R. . |
| 681366 | 8/1979 | U.S.S.R. . |

OTHER PUBLICATIONS

Bilgutay et al., "The Effect of Grain Size on Flaw Visibility Enhancement Using Split-Spectrum Processing", The American Society for Non-Destructive Testing, Materials Evaluation, 42, May 1984, pp. 808–814.

Klinman, et al., "Ultrasonic Prediction of Grain Size, Strength, and Toughness in Plain Carbon Steel", Materials Evaluation, Oct. 1980, pp. 26–32.

S. S. Lee, J. F. Smith and R. B. Thompson, "Inference of Crystallite Orientation Distribution Function Form the Velocities of Ultrasonic Plate Modes", *Nondestructive Characterization of Materials*, J. F. Bussiere, Ed. (Plenum Press, N.Y. in press) 1985.

R. Bruce Thompson, S. S. Lee, and J. F. Smith, "Angular Dependence of Ultrasonic Wave Propatation in a Stressed Orthorhombic Continuum; Theory and Application to the Measurement of Stress and Texture", J. Acoust. Soc. Am. 80(3), Sep. 1986, pp. 921–931.

R. B. Thompson, S. S. Lee, and J. F. Smith, "Relative Anistropic of Plane Waves and Guided Modes in Thin Orthohombic Plates: Implication for Texture Characterization", Ultrasonics 25, 133–138 (1987).

S. J. Wormley and R. B. Thompson, "A Semi-Automatic System for the Ultrasonic Measurement of Texture", in *Review of Progress in Quantitative Nondestructive Evaluation 6A*, D. O. Thompson and D. E. Chimenti, Eds. (Plenum Press, N.Y. 1987), p. 951.

*Primary Examiner*—Hezron E. Williams
*Assistant Examiner*—Louis M. Arana
*Attorney, Agent, or Firm*—Zarley, McKee, Thomte Voorhees & Sease

[57] ABSTRACT

A means and method for ultrasonic measurement of texture non-destructively and efficiently. Texture characteristics are derived by transmitting ultrasound energy into the material, measuring the time it takes to be received by ultrasound receiving means, and calculating velocity of the ultrasound energy from the timed measurements. Textured characteristics can then be derived from the velocity calculations. One or more sets of ultrasound transmitters and receivers are utilized to derive velocity measurements in different angular orientations through the material and in different ultrasound modes. An ultrasound transmitter is utilized to direct ultrasound energy to the material and one or more ultrasound receivers are utilized to receive the same. The receivers are at a predetermined fixed distance from the transmitter. A control means is utilized to control transmission of the ultrasound, and a processing means derives timing, calculation of velocity and derivation of texture characteristics.

24 Claims, 3 Drawing Sheets

SEMI-AUTOMATIC SYSTEM FOR ULTRASONIC MEASUREMENT OF TEXTURE

GOVERNMENT RIGHTS

This invention was made with government support under contract number W-7405-ENG-82 awarded by the Department of Energy. The Government has certain rights in the invention.

This is a continuation of copending application Ser. No. 197,763 filed on May 23, 1988, now abandoned.

BACKGROUND OF THE INVENTION (a) Field of the Invention

The present invention relates to measurement of texture of materials, and in particular, to a means and method for use of ultrasound to measure texture (b) Problems in the Art It is obviously advantageous to be able to discern the texture characteristics of certain materials. Texture properties of the material provide information helpful in deciding the use for the material, and perhaps, can indicate possible manufacturing changes which can desirably alter those characteristics.

Texture relates to a number of material properties such as hardness, grain size, ductility, strength, grain orientation, stress adaptability, and formability. A primary example of materials where texture characteristics are important is with respect to metals, and in particular, to rolled metal plates and sheets.

The most common forms of texture measurement utilize x-ray diffraction. These techniques most times require separation of random samples of the material so that they can be destructively tested. Furthermore, x-ray diffraction must be conducted in a laboratory setting with controlled environment, and takes significant amounts of time to produce results. Although more portable x-ray diffraction systems are being developed, they still require destructive break-down of samples and significant amounts of time. Moreover, x-ray diffraction produces valid results only with respect to near-surface layers of the material, even if the material is a relatively thin metal plate or sheet, and does not give information on texture for the entire cross-section of the material.

Current texture measurement procedures therefore can be improved upon. There is a real need for means and methods to derive reliable texture information from the entire cross-section of a material, and not just surface layers. Texture characteristics can change drastically between the surface and inner layers of the material.

Secondly, there is a real need for the ability to derive texture information without the significant time delays of x-ray diffraction, or the closely-related neutron diffraction techniques.

Third, there is a real need for a means and method for texture measurement which can be applied directly to, and contemporaneously with, the normal production or processing of the materials. For example, it would be highly advantageous to be able to derive texture information regarding rolled metal plate or sheet as it is being formed; and to do such monitoring non-destructively, and in the actual manufacturing environment of the plate or sheet. The elimination of destructive evaluation which must be done with special equipment in special laboratory environment, would greatly reduce cost, and would allow contemporaneous monitoring and alteration of manufacturing processes according to the measured texture results.

It is therefore a principal object of the present invention to provide a means and method for ultrasonic measurement of texture which overcomes or solves the problems and deficiencies in the art.

A further object of the present invention is to provide a means and method as above described, which can accurately derive texture information from a material.

A further object of the present invention is to provide a means and method as above described which is nondestructive.

A further object of the present invention is to provide a means and method as above described which can derive texture information quickly and efficiently.

A further object of the present invention is to provide a means and method as above described which can be operated in a wide variety of environments, including manufacturing and processing environments of the material being investigated.

A further object of the present invention is to provide a means and method as above described which can operate adequately notwithstanding environment changes such as in temperature.

These and other objects, features and advantages of the present invention will become more apparent with reference to the accompanying specification and claims.

SUMMARY OF THE INVENTION

A means and method for ultrasonic measurement of texture in materials, whereby texture measurement and information is nondesctructively, efficiently, and accurately derived in a short period of time. According to the method, ultrasonic energy is transmitted into the material, and received by two ultrasonic energy receiver means positioned at a fixed distance from each other and from the transmitter of the ultrasonic energy. The time between reception at each receiver is detected, and velocity of the ultrasonic energy through the material is calculated. By utilizing these velocity measurements in appropriate calculations, texture characteristics can be derived. Alternatively, one receiving transducer can be used and timing can take place between the transmitting and receiving transducer.

The means of the invention implements one or more sets of ultrasound transmitters and receivers. Each set consists of a transmitting transducer of ultrasound waves to direct the waves into the material, and at least one ultrasound receiving transducer, positioned at a predetermined distance from each other (if more than one receiving transducer), and positioned at a fixed, predetermined distance from the transmitter, to receive the ultrasound waves after transmission through the material. A timing means detects and measures the time the waves take between the transmitting and receiving transducers, or each of the receiving transducers of each set if two are used. A processor means utilizes the timing measurement to calculate velocity of the waves, and then derives the texture information or characteristics. Multiple sets of transmitters and receivers are used so that velocities can be measured for different plate modes of the rolled metal plate or sheet. Plate modes are explained in many of the references cited at the end of this specification, and are well known to those of ordinary skill in the art. ("Plate modes" is terminology from the field of physical acoustics meaning particular sets of elastic waves in thin material, while "plate" and "sheet" is terminology from the metals industry indicating thin metal material, sheet being thinner than plate).

The invention functions by incorporating mathematical formulations which produce texture characteristics estimations based upon knowing velocities of ultrasonic waves in the different modes through the material. These mathematical formulations are set forth in a co-pending, co-owned application, entitled "Method for Ultrasonic Measurement of Texture", by R. Bruce Thompson, Jack S. Smith, Seuk Lee, and Yan Li, U.S. Ser. No. 188,495, now U.S. Pat. No. 4,899,589, filed Apr. 29, 1988, which is incorporated herein by reference.

The processing means and steps of the invention can control operation of and production of the transmitted ultrasonic waves, and can record, display, or otherwise further process the results for advantageous use. The invention therefore allows texture information to be derived which meets the above-stated objects, and which improves over the present state of the art.

DETAILED DESCRIPTION OF THE PREFERRED EMBODIMENT

With respect to the drawing, FIG. 1, a preferred embodiment of the invention will now be described. Components of the preferred embodiment depicted in FIG. 1 will be identified by reference numerals, which will be used throughout this description.

Figure 1:
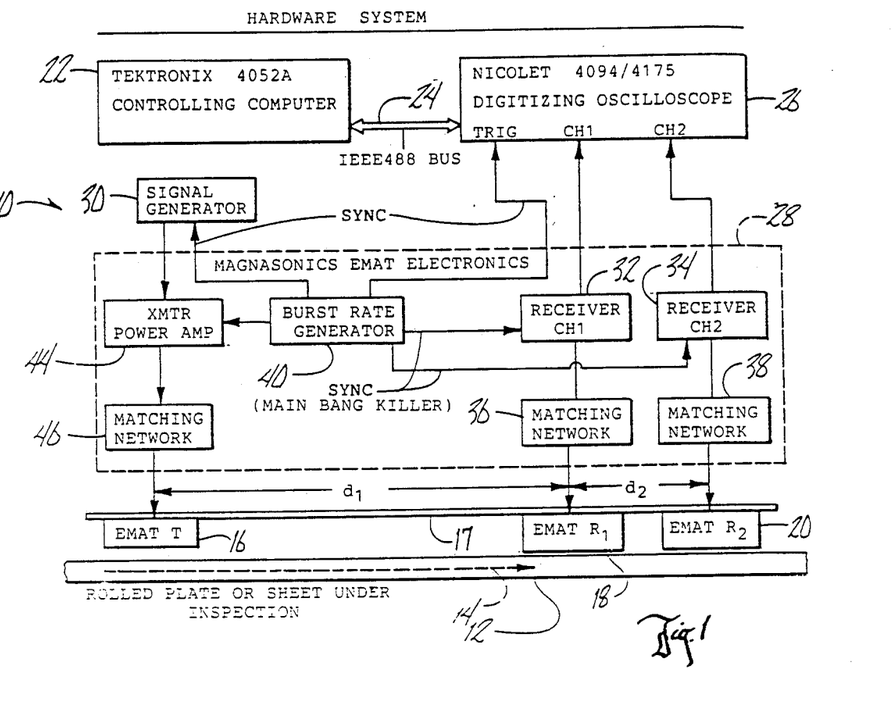
FIG. 1 is a schematic representation of a preferred embodiment of the invention, as applied to rolled metal plate.

FIG. 1 depicts generally a semi-automatic system 10 for ultrasonic measurement of texture of materials. The particular material under inspection in this preferred embodiment is rolled metal plate or sheet 12. Arrow 14 depicts the rolling direction of plate or sheet 12. Plate or sheet 12 is continuous and is passing by system 10 at a controlled (but usually unknown) speed such as could be found in a manufacturing facility of rolled metal plate or sheet. The rolling speed of the plate or sheet is not critical to the operation or accuracy of the invention. It is to be understood, however, that the invention also operates with regard to stationary materials.

In the preferred embodiment, two sets of ultrasound transducers are utilized to transmit and receive ultrasound for purposes of velocity measurements. Each set is particularly configured for a different plate mode ($S_n$, $A_n$ and $SH_n$ where $n=0,1,2,3\ldots$) and have appropriately adjusted matching networks for each transducer of each set for its particular function. Otherwise, each set operates essentially the same, but for the different modes, and therefore for purposes of simplicity, only one set will be described. $S_n$ or S refers to extensional or symmetric Lamb plate mode of ultrasound, $A_n$ or A refer to flexural or antisymmetric Lamb plate modes of ultrasound, whereas $SH_n$ or SH refers to shear horizontal plate mode of ultrasound. It is to be understood that operation of transducers for $S_n$, $A_n$ and $SH_n$ modes, and their appropriate matching networks, is known within the art.

With respect to one set of transducers, a transmitter 16 of ultrasonic energy is positioned adjacent plate or sheet 12. In the preferred embodiment, transmitter 16 comprises an electromagnetic acoustic transducer (EMAT), such as is well known within the art. Transmitter 16 is fixedly secured to the underside of a substantially rigid member, such as steel rule 17, which is adjustably positionable with respect to the plate and appropriately aligned so that transmitter 16 can direct ultrasound waves to the plate in different angular orientations. Steel rule 17 is positioned so that the ultrasound waves from transmitter 16 will enter and propagate along plate or sheet 12. Steel rule 17, in the preferred embodiment, is adjustable so that its center longitudinal axis can be oriented between 0°–90° with respect to rolling direction. In the preferred embodiment, 0°, 45°, and 90° are selected.

In the preferred embodiment, a first ultrasound receiver 18 and a second ultrasound receiver 20, both adjacent to plate 12, are also fixedly secured to the underside of steel rule 17 and are in appropriate operative orientation to receive ultrasound waves transmitted from transmitter 16 and propagated through plate or sheet 12. Receivers 18 and 20 are, in the preferred embodiment, also electromagnetic acoustic transducers (EMATs), functioning in the "receive" or "catch" mode, such as is known in the art. Transmitter 16 is operating in the "transmit" or "pitch" mode.

Figure 2:
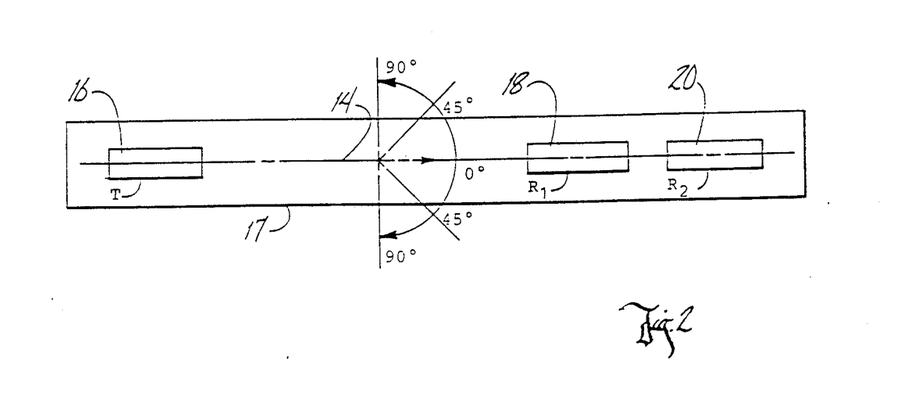
FIG. 2 is a bottom view schematic of a one transmitter and two receiver set of transducers attached to the underside of a rigid member and depicts the angular adjustability of the rigid member with respect to the rolling direction of the metal plate.

Receivers 18 and 20 are positioned a predetermined distance $d_2$ from one another and are aligned along the longitudinal axis of steel rule 17. Likewise, receiver 18 is positioned a predetermined distance $d_1$ from transmitter 16. Transmitter 16 and receivers 18 and 20 are therefore angularly stationary with respect to each other but are adjustable as a set on steel rule 17 with respect to the surface and rolling direction 14 of plate or sheet 12 so that, as a set, they are adapted to receive ultrasonic waves at various angular orientations to plate or sheet 12 (see FIG. 2). It is to be again understood that timing measurements could also be made by timing the ultrasound between transmitter 16 and a single receiving transducer.

Operation of transmitter 16, and receivers 18 and 20 is controlled by burst rate generator 40. Digitizing oscilloscope 26 receives information from the receiving transducers 18 and 20 through appropriate circuitry and prepares it for processing by computer 22. Computer 22 communicates through data bus 24 to digitizing oscilloscope 26. It is to be understood that alternatively, analog components can be used to receive the signals from the receiving transducers 18 and 20 and can be used to derive velocity information.

Broken line 28 encloses components which interface between transducers 16, 18, 20 and oscilloscope 26, and also with signal generator 28, and essentially provide the means for controlling operation of transmitter 16 and receivers 18 and 20 according to the purposes of the invention. All of the components inside broken line 28 are conventional, known in the art components. Receivers 32 and 34 each contain electronic circuitry which captures the voltage signals produced by receiving transducers 18 and 20 from the received ultrasonic waves and prepares them for introduction to oscilloscope 26. Receivers 32 and 34 are selected to be appropriate for the frequencies and other parameters of the ultrasound and signals received, and it is to be understood that these signals are also amplified by receivers 32 and 34 to prepare them for passage to and processing by oscilloscope 26. For purposes of the preferred embodiment, receiver circuits 32 and 34 output signals designated as channel 1 and channel 2, respectively. These outputs are then connected operatively to the first and second channel inputs on oscilloscope 26. It is to be understood that alternatively a single receiver circuit could be utilized by switching its input alternatingly between receiving transducers 18 and 20.

The burst rate generator 40 is the basic controlling unit for the EMAT electronics. Generator 40 is pre-settable to direct production of signals to send out a synchronization or sync signal which serves to trigger digitizing oscilloscope 26, trigger signal generator 30, and gate power amp 44, and to temporarily inhibit receiving circuits 32 and 34. This thus activates each transmitter 16, and synchronizes or gates the operation of corresponding receiving transducers 18 and 20, and receivers 32 and 34.

As is shown in FIG. 1, synchronization lines emanate from generator 40 to signal generator 30, power amp 44, receivers 32 and 34, and scope 26. The signal along each sync line is independently adjustable according to desire.

To operate the invention, burst rate generator 40 is set to be prepared to send desired sync signals to the various components according to desired time or other values. Signal generator 30, computer 22, and scope 26 are also turned on and prepared for functioning. Appropriate software is pre-installed in computer 22. Burst rate generator 40 is then turned on. In the preferred embodiment, generator 40 directs signal generator 30 to produce short bursts (approximately 100 per second) of radio frequency (rf) signals (at approximately 0.45 megahertz (Mhz)). On a sync signal from generator 40, power amp 44 passes and amplifies each burst and sends it to matching network 46, which has been set to impedance match transmitting transducer 16. EMAT T 16 then, as well known in the art, excites a desired mode of sound in plate 12, according to the configuration of EMAT T 16 (in the preferred embodiment $S_n$ or $SH_n$ where $n = 0, 1, 2 \ldots$).

At the same time, generator 40 is sending sync signals to receivers 32 and 34, which temporarily "turns off" those items to prevent saturation due to the transmitted ultrasound. The "sync" signal from burst rate generator 40 to receiving circuits 32 and 34 thus serves as a "main bang killer", temporarily disabling or inhibiting circuits 32 and 34. This inhibiting lasts only a short enough time (on the order of a microsecond) so circuits 32 and 34 do not become overloaded or saturated by the initial "main bang" (large radio frequency signal) of transmitter 16, but are turned back on well before they are needed to receive the ultrasound signals needed for timing measurements, which is generally 10 microseconds or more after the "main bang". EMATs $R_1$ and $R_2$ (reference numerals 18 and 20) are configured for the plate mode of EMAT T 16, to pick up or "receive" that particular mode ultrasound, change those energy values into electrical signals, and pass those signals through corresponding matching networks 36 and 38 (for impedance matching again) to receivers 32 and 34. Matching networks 32 and 34 are adjustable to allow accurate impedance matching. Receivers 32 and 34 collect the signals from EMATs 18 and 20, amplify those signals and pass them to scope 26, where they are digitized and displayed, if desired. Scope 26 is synchronized by the sync signal also, and allows the received signals to be processed by the digital computer 22. If analog processing alternatively is used, the information from receiving circuits 32 and 34 preferably must ultimately get to computer 22 or another computer system in a digital format.

Signal generator 30 is an independent component outside of the circuitry contained within broken line 28. In the preferred embodiment, the components within broken line 28 can be comprised of Magnasonics EMAT electronics devices (Albuquerque, N. Mex.). Computer 22 can be a Tektronix 4052A computer, with oscilloscope 26 being Nicolet 4094/4175 Digitizing Oscilloscope. A conventional IEEE488 bus can connect computer 22 and oscilloscope 26. Matching networks 36 and 38 are known in the art components, and are operatively connected between receiving transducers 18 and 20 and receiver circuits 32 and 34. Matching networks 36, 38 and 46 "tune" or impedance match both the EMATs and their connecting cables.

It is again emphasized that FIG. 1 depicts one set only of transmitter/receiver(s) combination. As will be further discussed, additional sets of a transmitter and first and second receivers, fixed and positioned at predetermined distances from each other, but adjustable as a set with respect to rolling direction 14, can be utilized to take measurements for different plate modes.

It is to be understood that for different plate modes, different EMATs are utilized, and the matching networks are correspondingly adjusted for impedance matching. Alternatively, two complete different sets of EMATs and EMAT electronics could be used for different plate modes.

Figures 3, 4:
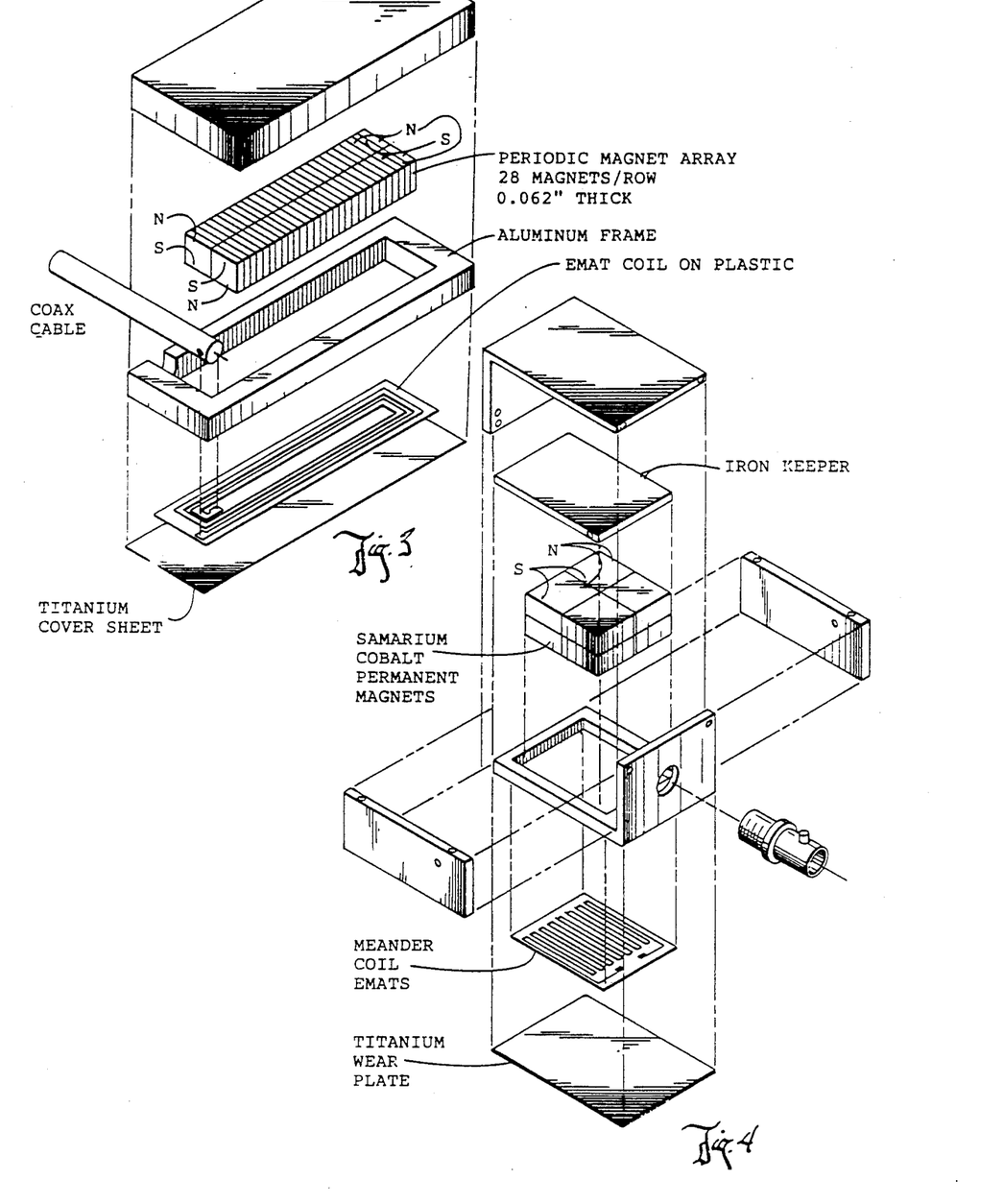
FIG. 3 is an exploded perspective view of one embodiment of an EMAT designed to excite and detect ultrasonic SH (shear horizontal) waves.
FIG. 4 is an exploded perspective view of an embodiment of an EMAT designed to excite S (extensional or Lamb) ultrasonic waves.

FIGS. 3 and 4 depict two embodiments of EMATs which could be used for measurements in the $S_o$ and $SH_o$ modes. These EMATs are well known within the art and are not a part of this invention. Their operation is also well known within the art. As can be seen in FIG. 3, an EMAT designed to excite and detect ultrasonic SH (shear horizontal) waves is shown. This particular embodiment is configured to excite and detect wave lengths of $\lambda = 0.124$ inches. It utilizes a periodic permanent magnet and an EMAT coil to generate eddy currents within the material to excite a shear horizontal mode of sound when used as a transmitter, and detects the same when used as a receiver.

FIG. 4 shows an embodiment of an EMAT designed to excite $S_n$ (extensional or Lamb) ultrasonic waves. It utilizes a permanent magnet with a meander type of coil to accomplish the same.

Figure 5:
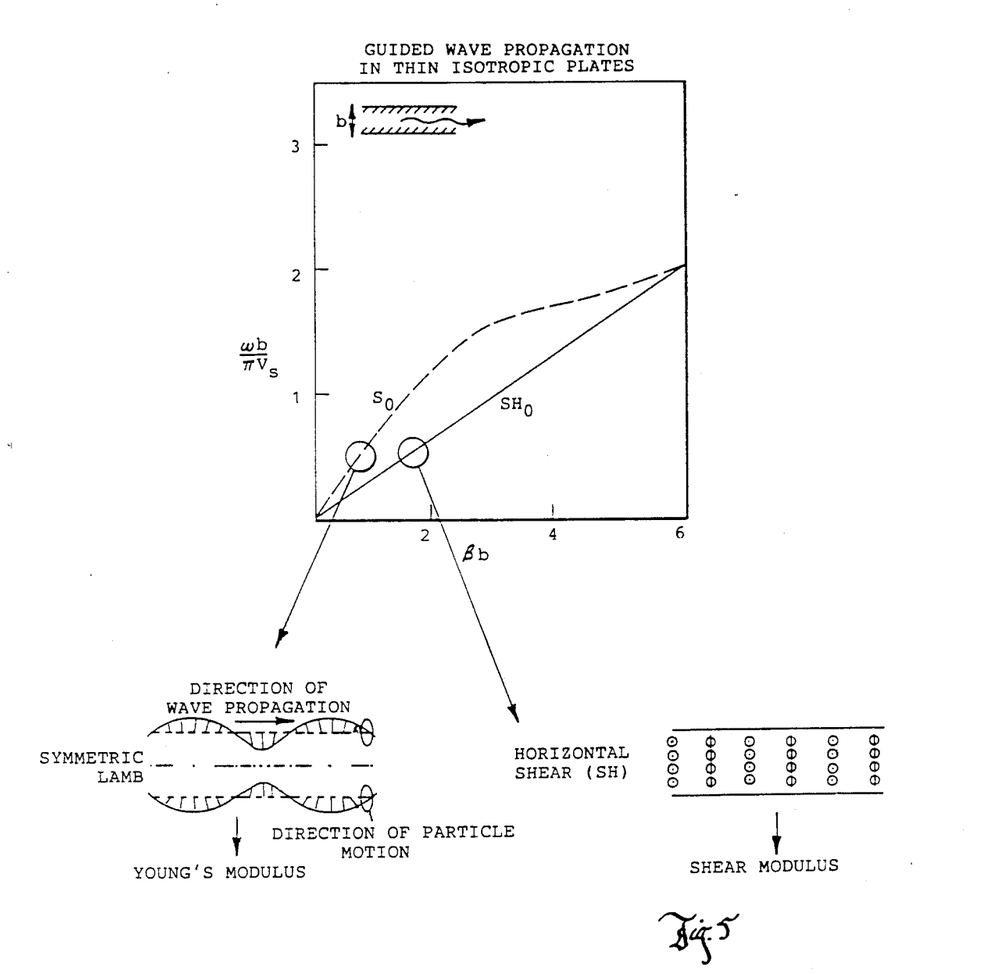
FIG. 5 is a graphic representation of guided wave propagation in thin isotropic plates for the $S_o$ and $SH_o$ modes

FIG. 5 depicts in graphic form guided wave propagation in thin isotropic plates in the $S_o$ and $SH_o$ modes. It is to be understood that in the $SH_o$ mode the system is essentially measuring the anisotropy of the shear modulus for deformations in the plane of the plate. In the $S_o$ mode, the anisotropy of a quantity is measured which can be qualitatively characterized as Young's Modulus. This measurement requires that the wavelength be large with respect to the plate thickness. As previously stated, the $S_o$ mode is also commonly referred to as the fundamental symmetric Lamb mode.

It is to be understood that in the preferred embodiment, receiving transducers 18 and 20 are spaced between 12 and 16 centimeters apart. All of the EMATs utilized in the preferred embodiment of the present invention are on the order of a rectangular shape. They are also positioned so as to gently abut or be closely adjacent to the surface of the rolled plate. In industrial applications they can be positioned approximately 1/1000th of an inch from plate 12. They would then ride on a thin film of air so that they do not actually abut the plate.

It is also to be understood that the construction of the matching networks of the preferred embodiment of the present invention is as follows. For transmitting EMATs, matching network 46 comprises a variable output transformer between the amplifier 44 and the EMAT 16. Additionally, a variable capacitor is placed between the transformer and EMAT 16 and in the preferred embodiment, is between 0 and 0.099 microfarads; adjustable in 0.001 microfarad graduations. On the other hand, the matching networks for the receiving EMATs 18 and 20 consist simply of an adjustable capacitor as previously described.

It can therefore be seen that the embodiment of FIG. 1 presents a means for semi-automatically controlling generation of pulses of ultrasonic energy from transmitter 16 which is introduced to plate 12. Burst rate generator 40 simultaneously instigates the transmitted pulse, and triggers oscilloscope 26. It further sends a "main bang" killer to receiver circuit 32, and to receiver circuit 34. The main bang killer inhibits both receivers to prevent saturation during the transmit time. Receiving transducers 18 and 20, and the following components then provide information to oscilloscope 26 and computer 22 so that timing measurements can be taken between EMATs 18 ($R_1$) and 20 ($R_2$) Because distance $d_2$ is known by pre-calibration, computer 22 can then compute velocity of the ultrasound waves through plate 12. Thus, it is to be understood that distance $d_2$ is sufficient to allow for valid time measurements to an acceptable level of accuracy, such as is known in the art. If timing is accomplished between transmitter 16 and a single receiving transducer, distance $d_1$ is pre-calibrated to derive velocity of the ultrasound.

The method of operation of the invention utilizes the processes set forth in co-pending, co-owned application entitled "A Method for Ultrasonic Measurement of Texture", by Thompson, Smith, Lee, and Li, Serial No. 188,495 now U.S. Pat. No. 499,589, filed Apr. 29, 1988, incorporated herein by reference. It is there disclosed that mathematical formulations have been developed, which with improved accuracy, can estimate the texture characteristics of rolled metal plate from velocity measurements of ultrasound.

It is known that rolled metal plate has basically a crystallite structure. The structure has been modeled as a continuum, having macroscopic orthotropic symmetry, which is depicted in the form of three mutually perpendicular mirror planes. It has also been disclosed that a relationship exists between what are called the macroscopic elastic constants of a rolled metal plate, and the coefficients of an expansion of the crystallite orientation distribution function (CODF) in terms of generalized Legendre functions. C. M. Sayers, "Ultrasonic Velocities in Anisotropic Poly-Crystalline Aggregates", J.Phys. D 15, 2157-2167 (1982). U.S. patent application, Thompson, Smith, Lee and Li, Ser. No. 188,495, now U.S. Pat. No. 4,899,589, incorporated by reference, discloses that the coefficients of the CODF function can be derived from velocity measurements of ultrasonic plate modes.

In the preferred embodiment, the plate modes of interest are $SH_O$ and $S_O$, whereas the coefficients of interest are $W_{400}$, $W_{420}$, and $W_{440}$. It is to be understood that $W_{400}$, $W_{420}$, and $W_{440}$ are required for cubic metals such as copper, aluminum, and steel, but more coefficients are required for hexagonal metals, such as titanium. The invention can be easily extended for such materials according to the principles disclosed herein. The degree of preferred orientation of crystallites of the metal plate are quantified by a CODF represented by $\omega(\xi, \psi, \phi)$, where the arguments are Euler angles describing the orientation of crystallites with respect to the sample axes. The orientation distribution coefficients, $W_{lmn}$ are predicted as follows:

$$W_{440} = \frac{\sqrt{35}\,\rho}{16\,\pi^2 C} [SH_o^2(45°) - SH_o^2(0°)]$$

$$W_{440} = \frac{\sqrt{35}\,\rho}{32\,\pi^2 C} [S_o^2(0°) + S_o^2(90°) - 2V_{S_o}^2(45°)]$$

$$W_{420} = \frac{7\sqrt{5}\,\rho}{32\,\pi^2} (1 + 2P/L)C\,[S_o^2(90°) - V_{S_o}^2(0°)]$$

$$W_{400} = \frac{35\sqrt{2}\,\rho}{16\,\pi^2 C} [V_{SH_o}^2(45°) + V_{SH_o}^2(0°) - 2T/\rho]$$

$$W_{400} = \frac{35\sqrt{2}\,\rho}{32\,\pi^2[3 + 8(P/L) + 8(P/L)^2]C} [V_{S_o}^2(0°) +$$

$$V_{S_o}^2(90°) + 2V_{S_o}^2(45°) - 4(L - P^2/L)\rho]$$

Conventionally, the CODF is set forth as a series of generalized Legendre functions ($Z_{lmn}$). R. J. Rose, J Appl. Phys., 37 (1966), p. 2069.

A conventional CODF can be expressed as:

$$w(\xi,\psi,\phi) = \sum_{l=0}^{\infty} \sum_{m=-l}^{l} \sum_{n=-l}^{l} W_{lmn}\, Z_{lmn}(\xi)\, e^{-im\psi} e^{-in\phi}.$$

For cubic crystallites, symmetry dictates that the lowest order independent coefficients are $W_{000} = \frac{1}{2}\sqrt{2\pi^2}$ (a normalization constant), and $W_{400}$, $W_{420}$, and $W_{440}$. Following the Voigt procedure for averaging elastic constants, the polycrystalline elastic constants, $C_{IJ}$, of the orthohombic plate may be expressed in terms of these four $W_{lmn}$ coefficients and the single crystal elastic constants, $C_{IJ}°$. [See again, C. M. Sayers article noted above]. Typical results are:

$$C_{44}' = C_{44}^0 + C^o [1/5 - 16/35\,\sqrt{2}\,\pi^2\,(W_{400} - \sqrt{(5/2)}\,W_{420})]$$

$$C_{55}' = C_{55}^0 + C^o [1/5 - 16/35\,\sqrt{2}\,\pi^2\,(W_{400} + \sqrt{(5/2)}\,W_{420})]$$

$$C_{66}' = C_{66}^0 + C^o [1/5 + 4/35\,\sqrt{2}\,\pi^2\,(W_{400} - \sqrt{70}\,W_{440})],$$

with similar relationships available for the remaining six independent elastic constants.

These elastic constants, and hence the $W_{lmn}$ can be inferred from measurements of ultrasonic wave speeds.

$SH_o(\theta)$ represents the velocity of the fundamental horizontally polarized shear mode and $S_o(\theta)$ represents that of the fundamental symmetric Lamb mode, sometimes referred to as the extensional mode.

It has been determined that velocity of two ultrasonic plate modes ($S_0$ and $SH_0$) must be measured in three propagation directions in order to determine the coefficients $W_{400}$, $W_{420}$, and $W_{440}$. This requirement is derived from the previous equations. Therefore, in the preferred embodiment of the present invention, velocity measurements are taken at 0°, 45° and 90° with respect to the rolling direction of plate 12. It is further preferred that these three measurements be taken by one set of transmitters 16 and receivers 18 and 20 for the $S_o$ mode, and an additional set of transmitters 16 and receivers 18 and 20 for the $SH_o$ mode.

Absolute velocities of the ultrasonic waves measured are obtained using this method. It is to be understood that EMAT transducers are utilized because of their couplant free operation and their ability to operate in a high temperature environment, which is necessary if system 10 is used directly in the manufacturing, production, or process control of metal rolled plate 12. However, other types of ultrasound transmitters and receivers can be used according to the invention.

In the preferred embodiment, ultrasonic velocity is determined by measuring the time difference between two received ultrasonic bursts by digital or analog implementations of zero-crossing, cross-correlation techniques or Fourier transform phase techniques. It is to be understood that in the preferred embodiment, frequency of the bursts is at rf (radio frequency). It is further to be understood that because many points on the wave form contribute to the velocity determination, a precise time difference measurement is obtained.

Oscilloscope 26 can also serve to convert the signals received by it from analog-to-digital. The preferred Nicolet Digitizing Scope 36 can digitize 8K (8,000) points per channel with a spacing as small as 2ns (nanoseconds) per sample point, capturing the complete burst of rf in each channel.

The included preferred embodiment is given by way of example only, and not by way of limitation to the invention, which is solely described by the claims herein. Variations obvious to one skilled in the art will be included within the invention defined by the claims.

Further background references regarding ultrasound propagation and its relationship to material texture are set forth below:

R. B. Thompson, J. F. Smith and S. S. Lee, *Nondestructive Evaluation of Microstructure for Process Control*, H. N. G. Wadley, Ed., ASM, Metals, Park, OH 1986, pp. 73.

R. Bruce Thompson, S. S. Lee, and J. F. Smith, "Angular Dependence of Ultrasonic Wave Propagation in a Stressed Orthorhombic Continuum; and Theory and Application to the Measurement of Stress and Texture", J. Accoust. Soc., Am, 80(3), Sept. 1986, pp. 921.

A. V. Clark, Jr., A Govada, R. B. Thompson, G.V. Blessing, P. P. Delsanto, R. B. Mignogna, and J. F. Smith, "The Use of Ultrasonic for Texture Monitoring in Aluminum Alloys", these proceedings.

R. F. Fields, National Bureau of Standards, private communication.

J. F. Smith, G. A. Alers, P. E. Armstrong, and D. T. Eash, "Separation and Characterization of Stress Levels in Metal Sheet and Plate: I. Principles of Initial Test":, J. Non-destr. Eva., 157–163 (1984).

J. F. Smith, R. B. Thompson, D. K. Rehbein, T. J. Nagel, P. E. Armstrong, and D. T. Eash, "Illustration of Texture with Ultrasonic Pole Figures", ibid.

*Textures in Non-Ferrous Metals and Alloys*, M. D. Merchant, and J. G. Morris, Ed. (The Metalurgical Society, Warrendale, Pa. 1985).

*Formability and Metallurgical Structure*, A. K. Sachdev and J. D. Embury (The Metallurgical Society, Warrendale, Pa. (1987). *Proceedings of ICOTOM-8*, J. S. Kallend and F. Koch, Ed, in preparation (Conference held Sept., 1987, Sante Fe, N. Mex.).

A. V. Clark, Jr., A. Govada, R. B. Thompson, J. F. Smith, G. V. Blessing, P. O. Delsanto, and R. B. Mignoggna, *Review of Progress in Quantitative Nondestructive Evaluation 6B*, D. O. Thompson and D. E. Chimenti, Eds. (Plenum Press, New York, 1987), p. 1515.

C. S. Barrett *Structure of Metals* (McGraw-Hill, New York, 1943).

H. J. Bunge *Texture Analysis in Materials Science, Mathematical Methods*, (Butterworth, London, 1982).

S. Mathies, G. W. Vmel, and K. Helming *Standard Distribution in Texture Analysis*, Vol. 1, (Akademie Verlag, Berline, 1987).

C. O. Ruud, "Application of Position Sensitive Scintillation Detector to Nondestructive X-ray Diffraction Characterization of Metallic Components", in Nondestructive Methods for Material Property Determination, C. O. Ruud and R. E. Green, Eds., (Plenum, N.Y. 1983).

R. B. Thompson, S. S. Lee, and J. F. Smith, "Relative Anistropic of Plane Waves and Guided Modes in Thin Orthohombic Plates: Implication for Texture Characterization, Ultrasonic 25, 133–138 (1987).

S. S. Lee, J. F. Smith and R. B. Thompson, "Ultrasonic Techniques for the Quantitative Characterization of Texture", in Ref. 2, 177–192.

S. S. Lee, J. F. Smith and R. B. Thompson, "Inference of Crystallite Orientation Distribution Function form the Velocities for Ultrasonic Plate Modes", Nondestructive Characterization of Materials, J. F. Bussiere, Ed. (Plenum Press, N.Y., in press).

R. B. Thompson, J. F. Smith, S. S. Lee and G. C. Johnston, "A Comparison of Ultrasonic and X-ray Determination of Texture in Cu and Al Plates (in preparation).

B. A. Auld, *Acoustic Waves and Fields in Solids*.

G. J. Davies, D. J. Goodwill and J. S. Kallend, Met. Trans. 3, 1627 (1972).

C. M. Sayers, "Ultrasonic velocities in anisotropic polycrystalline aggregates", J. Phys. D. 15, 2157–2167 (1982).

R. J. Rose, J. Appl. Phys., 37 (1966), p. 2069.

S. J. Wormley and R. B. Thompson, "A Semi-Automatic System for the Ultrasonic Measurement of Texture", in *Review of Progress in Quantitative Nondestructive Evaluation 6A*, D. O. Thompson and D. E. Chimenti, Eds. (Plenum Press, N.Y. 1987), p. 951.

S. S. Lee, J. F. Smith and R. B. Thompson "Inference of Crystallite Orientation Distribution Function form the Velocities of Ultrasonic Plate Modes", *Nondestructive Characterization of Materials*, J. F. Bussiere, Ed. (Plenum Press, N.Y. in press).

The present invention is applicable, in its preferred embodiment, to rolled plate such as stainless steel. However, it also has application to copper, aluminum, ferretic composites, and other similar cubic materials, as well as hexagonal materials such as titanium. Also, in the preferred embodiment, texture results can be derived in a matter of minutes (for example, 15 minutes).

What is claimed is:

1. An apparatus for semi-automatic ultrasonic measurement of texture in rolled metal sheet having a rolling direction, wherein the sheet has crystallite structure whose properties can be inferred from the velocities of ultrasonic plate modes, comprising:
   at least first ultrasonic transmitting transducer means for exciting ultrasonic energy in the form of a least one selected ultrasonic plate mode in the sheet, the transmitting transducer means including adjustable orientation means for selecting desired propagation directions with respect to the rolling direction of the sheet from a plurality of different propagation directions, the number of plate modes and directions being directly related to the type of crystallite structure of the sheet being analyzed;
   at least and second ultrasonic receiving transducer means for receiving the ultrasonic energy in a selected ultrasonic plate mode, each receiving transducer means including adjustment means for selecting desired angular orientation with respect to the sheet;
   each receiving transducer means for a particular plate mode positioned at a predetermined fixed distance from one another and from each transmitting transducer means for that plate mode allowing the measurement of both relative and absolute velocities of the ultrasonic energy;
   control means for operating each transmitting transducer means to generate the ultrasonic energy and each receiving transducer means for reception of the ultrasonic energy in the appropriate plate mode; and
   processing means for timing reception of the ultrasonic energy between any transducer means and for deriving texture characteristics of the sheet from relative and absolute velocity measurements of the ultrasonic energy by obtaining quantitative information defining preferred orientation of grains of the sheet.

2. The apparatus of claim 1 wherein the ultrasonic transducer means comprise electromagnetic acoustic transducers.

3. The system of claim 1 wherein the sheet includes rolled metal plate.

4. The system of claim 1 wherein the ultrasonic plate modes include $SH_n$, $S_n$, and $A_n$ modes, where n=0,1,2,3

5. The system of claim 1 further comprising two sets of the transmitting transducer means and ultrasonic receiving transducer means, one set for measuring ultrasonic wave velocities in the $SH_n$ mode where n=0,1,2,3 and one set for measuring ultrasonic wave velocities in the $S_n$ mode where n=0,1,2,3, ....

6. The apparatus of claim 1 wherein the texture characteristics include but is not limited to, one or more off the set comprising hardness, grain size, ductility, strength, grain orientation, stress adaptability, and formability and are obtained from further processing by the processing means.

7. The apparatus of claim 1 including a plurality of sets of receiver means and transmitter means for use with the system, the sets being operable both individually and in any combination, each set being adjustable to a desired orientation, excitation of a desired plate mode, and measurement of any of relative and absolute velocities to allow different ultrasonic characteristics to be individually or simultaneously derived.

8. The apparatus of claim 7 wherein each set consists of at least one transmitter means and receiver means, a means for adjusting the angular orientation of each set of transmitter means and receiving means with respect to the rolling direction of the sheet, and a timing means for independently taking time measurements for different propagation directions for the generated ultrasonic energy.

9. The apparatus of claim 8 including switching means for switching between the different sets.

10. The apparatus of claim 1 wherein the velocity measurements for one or more plate modes can be taken from the following set:
    three propagation directions in a first plate mode, and two propagation directions in a second plate mode;
    three propagation directions in a first plate mode, one in a second plate mode, and one in a third plate mode;
    two propagation directions in a first plate mode, two in a second plate mode, and one in a third plate mode;
    two propagation directions in a first plate mode, one in a second plate mode, one in a third plate mode, and one in a fourth plate mode; and
    one propagation direction in a first plate mode, one in a second plate mode, one in a third plate mode, one in a fourth plate mode, and one in a fifth plate mode.

11. The apparatus of claim 1 wherein the texture characteristics include one or more, but are not limited to, grain orientation and formability and are derived from further processing by the processing means.

12. The apparatus of claim 1 wherein the transmitting and receiving transducer means are controlled by the control means and texture characteristics are derived by the processing means from measurements of velocity of ultrasonic waves at one or more propagation directions with respect to modes $S_n$, $A_n$, and $SH_n$ of the plate, and by utilizing those measurements to determine aspects of a crystalline orientation distribution function.

13. The apparatus of claim 12 wherein the crystallite orientation distribution function comprises the equation:

$$w(\xi,\psi,\phi) = \sum_{l=0}^{\infty} \sum_{m=-l}^{l} \sum_{n=-l}^{l} W_{lmn} Z_{lmn}(\xi) e^{-im\psi} e^{-in\phi}$$

where w is the crystalline orientation distribution function expressed in terms of Euler angles $\theta$, $\psi$, $\phi$, $\xi = \cos\theta$ and $w_{lmn}$ are unknown coefficients that characterize texture with l,m,n being integers, these coefficients being determined from the ultrasonic velocity measurements, and $Z_{lmn}$ are generalized Legendre functions.

14. The apparatus of claim 13 wherein $W_{lmn}$, determined from the velocity measurements, are $W_{400}$, $W_{420}$, and $W_{440}$.

15. A method of analysis of texture in a metal sheet having a rolling direction comprising;
    passing the metal sheet at a controlled, but not necessarily known rate, by at least one set of ultrasonic transducers, each set coupling to a particular plate mode;

utilizing a transmitting transducer in each set of ultrasonic transducers to generate ultrasonic energy in the form of a plate mode through the metal sheet;

utilizing two or more receiving transducers in each set of ultrasonic transducers to receive the transmitted ultrasonic energy;

altering the angular orientation of each set of transducers with respect to the rolling direction as the metal sheet is moving, the number of alterations being directly related to the type of crystallite structure of the metal sheet being analyzed; and repeatedly measuring and correlating the time of travel of the ultrasonic energy between any two transducers of each set of ultrasonic transducers with texture parameters to derive texture characteristics by obtaining quantitative information defining preferred grain orientation of grains of the sheet, the measurement including calculation of relative and absolute velocities of the ultrasonic energy.

16. The method of claim 15 wherein velocity measurements are taken in one or more of $SH_n$, $A_n$, and $S_n$ plate modes.

17. The method of claim 16 wherein the transmitting and receiving transducer means are controlled by the control means and texture characteristics are derived by the processing means from measurements of velocity of ultrasonic waves at one or more propagation directions with respect to one or more $S_n$, $A_n$, and $SH_n$ of the plate, and by utilizing those measurements in a crystalline orientation distribution function.

18. The method of claim 17 wherein the crystallite orientation distribution function comprises the equation:

$$w(\xi, \psi, \phi) = \sum_{l=0}^{\infty} \sum_{m=-l}^{l} \sum_{n=-l}^{l} W_{lmn} Z_{lmn}(\xi) e^{-im\psi} e^{-in\phi}$$

where w is the crystalline orientation distribution function expressed in terms of Euler angles $\theta$, $\psi$, $\phi$, $\xi = \cos \theta$, and $w_{lmn}$ are unknown coefficients that characterize texture with l, m, n being integers, these coefficients being determined from the ultrasonic velocity measurements, and $Z_{lmn}$ are generalized Legendre functions.

19. The method of claim 18 wherein $W_{lmn}$, determined from the velocity measurements, are $W_{400}$, $W_{420}$, and $W_{440}$.

20. The method of claim 15 wherein the texture characteristics include one or more, but are not limited to, the set comprising hardness, grain size, ductility, strength, grain orientation, stress adaptability, and formability.

21. The method of claim 15 wherein the texture characteristics include one or more, but are not limited to, grain orientation and formability.

22. An apparatus for analyzing texture characteristics in a thin metal sheet having a rolling direction, comprising:

transmitter means for inducing ultrasonic energy in the form of a plate mode in a metal sheet in a plurality of directions in the general plane of said sheet;

first and second receiver means for reception of said energy in the form of a plate mode, and positioned a predetermined distance from said transmitter means to allow measurement of relative and absolute velocities of said energy; means for adjusting the angular orientation of the transmitter means and receiving means with respect to the rolling direction of said metal sheet;

timing means for measuring the time of travel of the ultrasonic energy between any of the transmitter means and receiving means, for each position of angular orientation of said transmitter means and said receiving means; and processing means for obtaining texture characteristics from the plurality of time measurements of said timing means derived from the transmittal and reception of said ultrasonic energy in the form of a plate mode in said metal sheet by obtaining quantitative information defining preferred orientation of grains of the metal sheet.

23. The apparatus of claim 22 wherein the timing means includes means for measuring time between transmission and reception of the ultrasound energy from the transmitter means to any receiver means.

24. The apparatus of claim 24 wherein the timing means includes means for measuring time between reception of the ultrasound energy at the first and second receiver means.

* * * * *